US009513278B2

(12) United States Patent
Vellutato, Jr.

(10) Patent No.: US 9,513,278 B2
(45) Date of Patent: *Dec. 6, 2016

(54) MICROBIAL AIR SAMPLER

(71) Applicant: Veltek Associates, Inc., Malvern, PA (US)

(72) Inventor: Arthur Vellutato, Jr., West Chester, PA (US)

(73) Assignee: Veltek Assoicates, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/807,642

(22) Filed: Jul. 23, 2015

(65) Prior Publication Data
US 2015/0330965 A1     Nov. 19, 2015

Related U.S. Application Data

(63) Continuation of application No. 13/930,967, filed on Jun. 28, 2013, now Pat. No. 9,121,845, which is a
(Continued)

(51) Int. Cl.
*G01N 1/22* (2006.01)
*G01N 33/497* (2006.01)
*G01N 1/00* (2006.01)

(52) U.S. Cl.
CPC .......... *G01N 33/497* (2013.01); *G01N 1/2208* (2013.01)

(58) Field of Classification Search
CPC ..................... G01N 1/2208; G01N 2001/2223; G01N 1/2273; G01N 1/26; G01N 2015/0261
See application file for complete search history.

(56) References Cited

U.S. PATENT DOCUMENTS 5,421,214 A    6/1995   Burgdorfer
5,831,182 A    11/1998  Swenson
(Continued)

FOREIGN PATENT DOCUMENTS

WO    WO 2009100184 A1    8/2009

OTHER PUBLICATIONS

Thermo Scientific Single Stage N6, Andersen Cascade impactor, Microbial, viable particle sizing sampler, Part of Thermo Fisher Scientific, Dec. 2009, Thermo Fisher Scientific Inc., 2 pgs.
(Continued)

*Primary Examiner* — Daniel S Larkin
*Assistant Examiner* — Jamar Ray
(74) *Attorney, Agent, or Firm* — Blank Rome LLP; Peter S Weissman

(57) ABSTRACT

An air sampler device has a top plate and a bottom plate, and receives a Petri dish between the top plate and the bottom plate. The top plate includes 283 substantially small holes. The bottom plate has a deepened center well formed in the top surface. Elongated slots are formed in the top surface which extend out from the well. The slots have distal ends which extend beyond the Petri dish. Air is drawn into the sampler by a vacuum tube through an air port which communicates with the center well. Air is pulled into the 283 holes in the top plate and strikes the capture material in the Petri dish. The air then travels up over the sides of the dish, into the distal ends, through the slots, and into the center well, where it exits out of the vacuum air port.

15 Claims, 3 Drawing Sheets

Related U.S. Application Data continuation of application No. 12/685,770, filed on Jan. 12, 2010, now Pat. No. 8,474,335.

(56) References Cited

U.S. PATENT DOCUMENTS

| | | | |
|---|---|---|---|
| 6,431,014 B1* | 8/2002 | Liu | G01N 1/2208 73/28.05 |
| 6,472,203 B1* | 10/2002 | Gallup | C12M 23/10 435/305.4 |
| 6,565,638 B1 | 5/2003 | Sugita et al. | |
| 6,911,343 B2 | 6/2005 | Schembri et al. | |
| 7,208,123 B2 | 4/2007 | Knollenberg et al. | |
| 7,421,911 B2 | 9/2008 | Desrochers et al. | |
| 8,474,335 B2* | 7/2013 | Vellutato, Jr. | G01N 33/497 73/28.05 |
| 9,121,845 B2* | 9/2015 | Vellutato, Jr. | G01N 33/497 |
| 2005/0058575 A1 | 3/2005 | Ishikawa et al. | |
| 2008/0087108 A1* | 4/2008 | Kreikebaum | G01N 1/2202 73/863.23 |
| 2010/0171625 A1 | 7/2010 | Calio | |

OTHER PUBLICATIONS

Copley Scientific, Quality Solutions fo Air Sampling & Particle Analysis, 2006 Edition, Copley Scientific AG, www.copleyscientific.com, pp. 1-27.

http://web.archive.org/web/20081010142807/http://www.sterile.com/pages/products/products-environmental-control-monitoring.htm Oct. 10, 2008.

http://web.archive.org/web/20081119084422/http://www.sterile.com/pages/products/environmental/sma-atrium.htm Nov. 19, 2006.

http://web.archive.org/web/20061123232739/htp://www.sterile.com/store/view-item-list.aspx?PlacementID=112 Nov. 23, 2006.

http://web.archive.org/web/20061123233126/http://www.sterile.com/store/item-pop-up.aspx?ItemID=SMA-316-18-1/4 Nov. 23, 2006.

Korean Office Action dated Jun. 28, 2016 issued in Korean Application No. 10-2016-7010503.

* cited by examiner

MICROBIAL AIR SAMPLER

RELATED APPLICATION

The present application is a continuation of and claims priority to U.S. patent application Ser. No. 13/930,967, filed Jun. 28, 2013, and entitled Microbial Air Sampler, which is a continuation of U.S. patent application Ser. No. 12/685,770, filed Jan. 12, 2010 (now U.S. Pat. No. 8,474,335), the entire contents of which is hereby incorporated by reference.

BACKGROUND OF THE INVENTION

1. Field of the Invention

The present invention relates to a microbiological gas sampler, and especially for sampling air. More particularly, the present invention relates to a microbial air sampler used in a controlled environment.

2. Background of the Related Art

A controlled environment is an area which is designed, maintained, or controlled to prevent particle and microbiological contamination of products. Controlled environments include, for example, clean rooms and clean hoods. There are different levels of cleanliness in clean rooms, generally in the range of a Class 100 room (i.e., a room having no more than 100 particles of 0.5 micron and larger, per cubic foot of air), to a Class 10,000 clean room.

Clean rooms are used for a variety of purposes, such as in the manufacture of pharmaceutical products and electronics, such as semiconductors. Often, clean rooms are used to work on extremely expensive and complex products, and it is not unusual that there be millions of dollars worth of product in a clean room at any given time. Clean rooms have to maintain a high level of cleanliness, or risk large financial losses. If a product being developed or manufactured in a clean room becomes contaminated, the entire product in the clean room must often be discarded.

Microbial air samplers are used to monitor the level of cleanliness (in terms of viable contamination) in a controlled environment. One or more samplers are positioned about the clean room to collect airborne particulates and organisms (or microorganisms) such as bacteria and fungi. Samplers that run at high flow rates permit air to enter the sampler at such high flow rates that loss of smaller particulates carrying microorganisms is normality (i.e., smaller particulates are not retained in the medium). At the same time high flow rate air samplers only sample for a short time period and relay on a short snapshot of the condition of the area. Samplers running at 28.3 LPM (liters per minute) must operate for a longer period of time than a unit running at 322 LPM. In doing this, they sample a broader spectrum of the drug fill time and present superior data as the sample time takes a larger snapshot of the operation. Samplers that run at 28.3 LPM also provide the ability to capture more smaller particulates that may be lost due to dynamic drag (or an umbrella affect) in higher flow rate units.

Air sampling systems are generally known, and an air sampling system is offered by Veltek Associates, Inc. known as SMA (Sterilizable Microbiological Atrium) Microbial Air Sampler System. One such system is shown in U.S. patent application Ser. No. 12/068,483, filed Feb. 7, 2008 and Ser. No. 12/402,738, filed Mar. 12, 2009, and the counterpart PCT published application WO2009/100184, the entire contents of which are hereby incorporated by reference. As noted in those applications, the air sampler system includes a controller connected to a vacuum pump to control the flow of air to air sampler devices located in the clean room.

A prior art air sampler device 5 is shown in FIGS. 1-2, which is offered by Veltek Associates, Inc. The air sampler device 5 includes a top plate 10 with openings 11 and a bottom plate 14. The bottom plate 14 has a circular ridge 16 on the top surface, which receives a Petri dish 12. The underside of the bottom plate 14 has a circular channel 20 (best shown in FIG. 2) which communicates with an air port 22. A metal cover plate 26 fits over the underside of the bottom plate 14, and a rubber gasket 24 is positioned between the bottom plate 14 and the cover plate 26 to provide an airtight seal. Screws are used to secure the cover plate 26 and gasket 24 to the bottom plate 14. In addition, a circular rubber gasket (not shown, but having the shape of a washer) is positioned on the top surface of the bottom plate 14 around the circular ridge 16 to create a substantially airtight seal between the bottom plate 14 and the top plate 10.

In operation, a vacuum tube is attached to the air port 22. Air is then sucked in through the openings 11 located in the top plate 10, so that the air strikes a test medium contained in the Petri dish 12. The air then exits the device 5 through holes 18 located on the ridge 16 of the bottom plate 14. The air passes into the channel 20, and exits through the air port 22. The entire device 5 is metal, except for the gasket 24, so that the device 5 can be sterilized by heat, steam, Vaporized Hydrogen Peroxide (VHP) or Ethylene Oxide (ETO). At the end of the testing period, the Petri dish 12 is removed and analyzed to determine the level of cleanliness of the clean room.

The Petri dish 12 has a diameter of about 3.5 inches. The top plate 10 has a diameter of 4.5 inches. There are twelve holes 11 positioned within about a circular area having a 3 inch diameter, and each hole 11 has a diameter of about 0.5 inches. The sides of the top plate 10 and the bottom plate 14 are smooth.

SUMMARY OF THE INVENTION

Accordingly, it is an object of the invention to provide a device for sampling viable cells in air. It is another object of the invention to provide a microbial air sampler having an improved design which is entirely sterilizable by heat, steam, VHP or Ethylene Oxide (ETO) and does not include a gasket. It is yet another object of the invention to provide a microbial air sampler which can accommodate current Petri dish shapes and sizes.

Accordingly, an air sampler device is provided having a top plate and a bottom plate, which receives a Petri dish between the top plate and the bottom plate. The top plate includes 283 substantially small holes. The bottom plate has a deepened center well formed in the top surface at the center of the bottom plate. Six elongated slots are formed in the top surface with proximal ends which extend out from the central well, and distal ends which extend beyond the Petri dish situated about the center of the bottom plate.

In operation, air is drawn into the sampler device by a vacuum tube through an air port which communicates with the center well. Air is pulled into the 283 holes in the top plate and strikes the capture material in the Petri dish. The air then travels up over the sides of the dish and into the distal ends of the slots of the bottom plate. The air then travels down the elongated slots beneath the dish, and enters the center well. The air is then sucked through the air passageway hole and exits out of the vacuum air port.

These and other objects of the invention, as well as many of the intended advantages thereof, will become more read-

DETAILED DESCRIPTION OF THE PREFERRED EMBODIMENTS

Figures 1, 2:
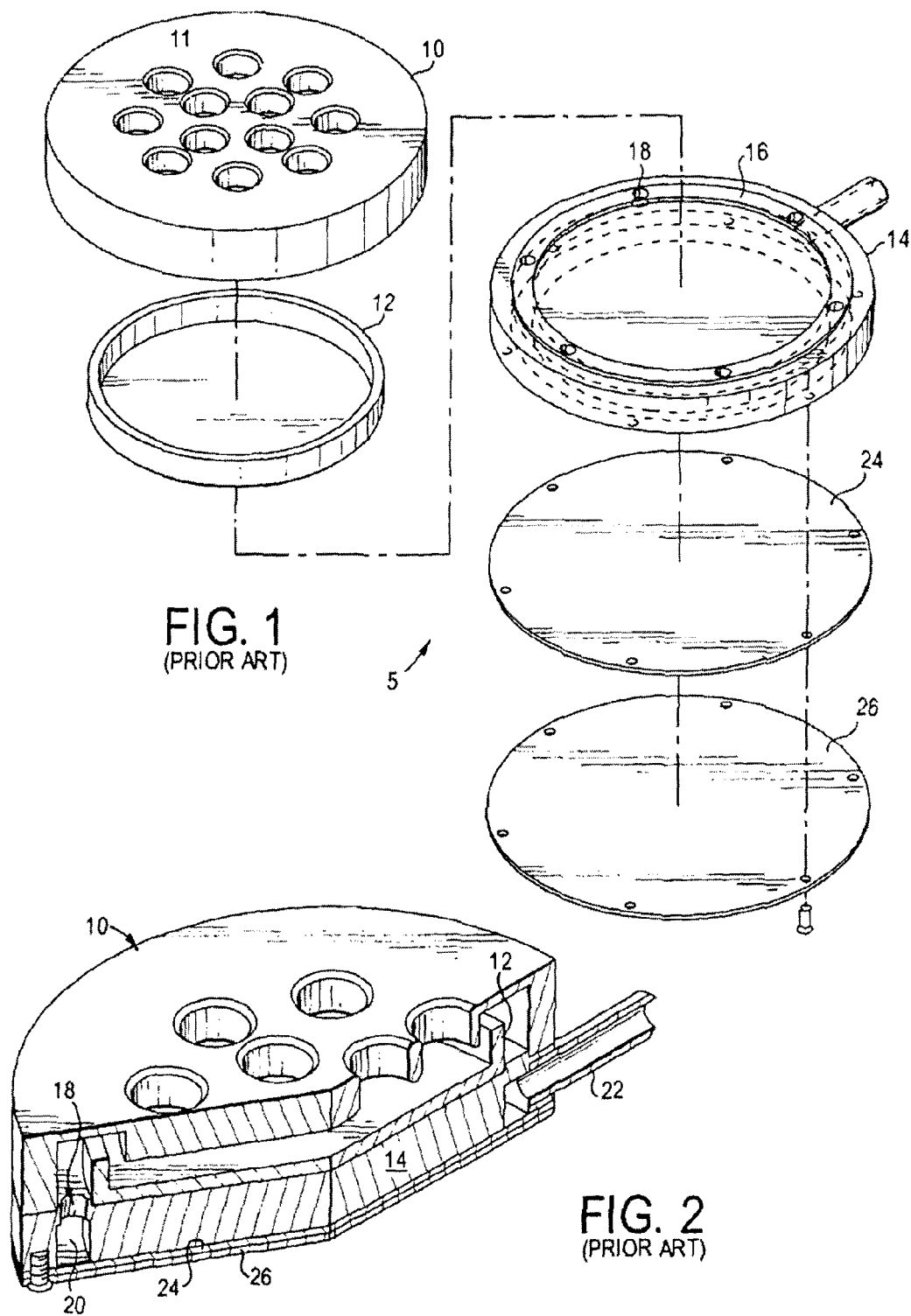
FIG. 1 is an exploded perspective view of the air sampler device in accordance with the prior art.
FIG. 2 is a cutaway perspective view of the air sampler device of FIG. 1 in accordance with the prior art.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose.

Figure 3:
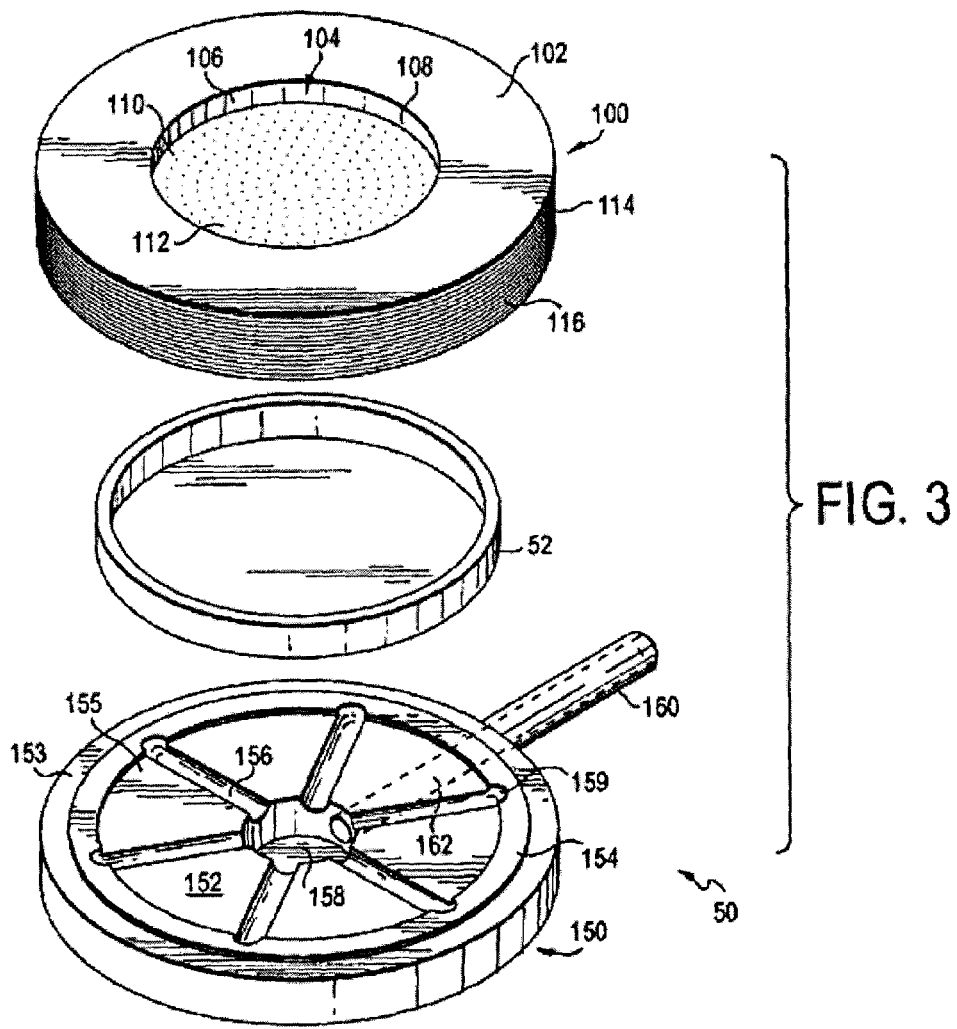
FIG. 3 is a top perspective view of the air sampler device in accordance with the preferred embodiment of the invention.

Turning to the drawing, FIG. 3 shows the air sampler device 50 in accordance with the preferred embodiment. The sampler 50 primarily includes a top plate 100 and a bottom plate 150, and a Petri dish 52 is positioned between the top plate 100 and the bottom plate 150. The sampler 50 is circular, though other suitable sizes and shapes can be utilized.

Figure 4:
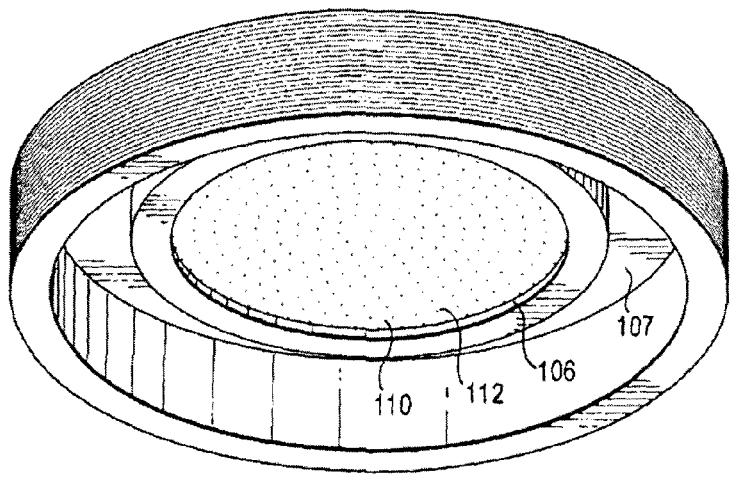
FIG. 4 is a bottom perspective view of the top plate of the air sampler device of FIG. 3.

The top plate 100 has a top surface 102 and a central depressed portion 104 which is depressed with respect to the top surface 102. The center of the top plate 100 is machined out to form the depressed portion 104 with a lip 108. And, as shown in FIG. 4, the underside of the top plate 100 is machined out to form a vent plate 110 and an inner wall 106. Accordingly, the vent plate 110 is integral with the top plate 100. There are two hundred and eighty-three (283) holes 112 formed in the vent plate. The inner wall 106 extends from the top surface 102 (FIG. 3) downward into the interior of the top plate 100. A channel 107 is formed between the inner wall 106 and the side wall 114 of the top plate 100 which act as a vacuum venture, whereby the vacuum is pulled through the top of the sampler, directly to the nutrient media and the up and over the Petri dish 52 sides.

Figure 6:
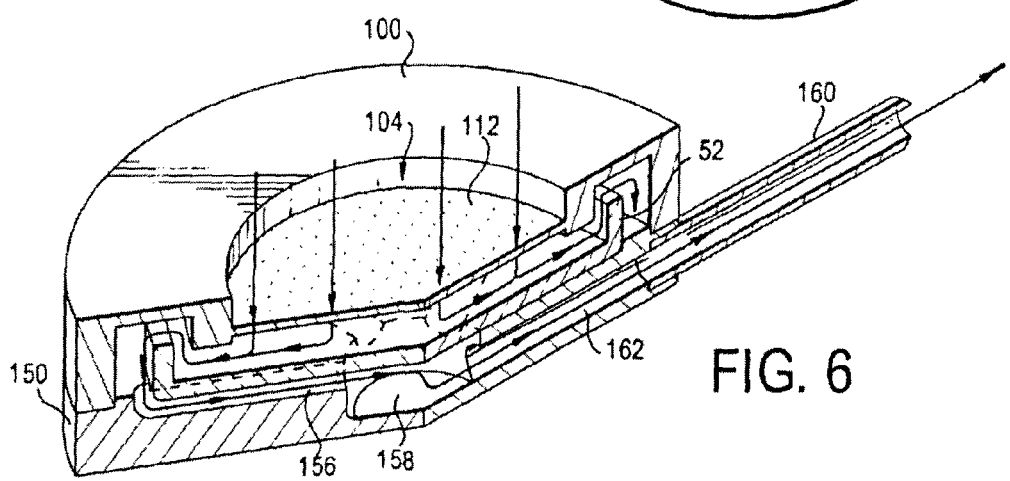
FIG. 6 is a cutaway top perspective view of an assembled air sampler device of FIG. 3 showing movement of air within the device; and, FIG. 7 is a top perspective view of an assembled air sampler device of FIG. 3.

The inner wall 106 extends downward into the center of the Petri dish 52 to further prevent (in addition to the ridge 154) the Petri dish from moving. The inner wall 106 is shorter than the sides of the Petri dish 52, so that the sides of the dish 52 contact the top of the channel 107 before the material in the Petri dish 52 contacts the inner wall 106. In addition, as best shown in FIG. 6, the inner wall 106 extends down into the Petri dish 52. The inner wall 106 prevents the sides of the dish 52 from moving, to keep the dish 52 properly centered on the bottom plate 150.

The top plate 100 has at least one outer side 114. The side 114 has ridges 116 extending around the outer circumference of the top plate 100. The ridges 116 make the top plate 100 easy to grip, so that a user can easily remove and replace the top plate 100 with respect to the bottom plate 150. In addition, the outer sides of the bottom plate are smooth, so that the user can easily differentiate between the bottom plate 150 and the top plate 100 when removing the top plate 100 from the bottom plate 150. The ridges 116 are particularly useful since users are often required to wear gloves (in addition to garments, hoods, and booties) at all times while inside the clean room. These features allow the top plate 100 to be easily lifted off of the bottom plate 150 without disturbing the bottom plate 150.

The bottom plate 150 has a top surface 152, and a ridge 154 extending upward from the top surface 152 at a distance from the outer edge of the bottom plate 150. The ridge 154 creates an outer shelf 153 which receives the side 114 of the top plate 100. The outside lip of the ridge 154 prevents the side 114 of the top plate 100 from moving off of the bottom plate 150. The ridge 154 also defines a receiving portion 155 which receives the Petri dish 52. The inside lip of the ridge 154 prevents the dish 52 from moving and keeps the dish 52 centered with respect to the bottom plate 150 and the holes 112 in the vent plate 110 of the top plate 100. Accordingly, the ridge 154 ensures that air coming in through the holes 112 in the vent plate 110 come into contact with the material in the Petri dish 52.

A deepened central well 158 is also formed in the top surface 152 at the center of the bottom plate 150. Six elongated slots 156 are formed in the top surface 152 at the receiving portion 155. The elongated slots 156 extend out from the central well 158 through the receiving portion 155 and the distal ends 159 of the slots 156 extend partly (approximately halfway) into the ridge 154. Thus, when the dish 52 is positioned on the top surface 152 of the bottom plate 150, the dish 52 covers the center well 158 and the slots 156, but does not cover the distal ends 159. The slots 156 have a rounded cross section (which is substantially a half-circle), and the distal ends 159 are also rounded, which facilitates air travel and prevents particles from clogging the slots 156. Accordingly, air can enter the distal ends 159 and travel in the slots 156 beneath the dish 52 into the center well 158. The bottom of the well 158 is rounded to meet up with the side of the well 158, such that the well 158 does not have hard corners and the air can travel freely without the corners collecting debris.

A vacuum air port 160 is positioned at the side of the bottom plate and communicates with an air hole 162. The air hole 162 extends through the bottom plate 150, from the air port 160 to the center well 158. The vacuum air port 160 connects to a vacuum tube 170 to draw air through the sampler 50.

Figure 5:
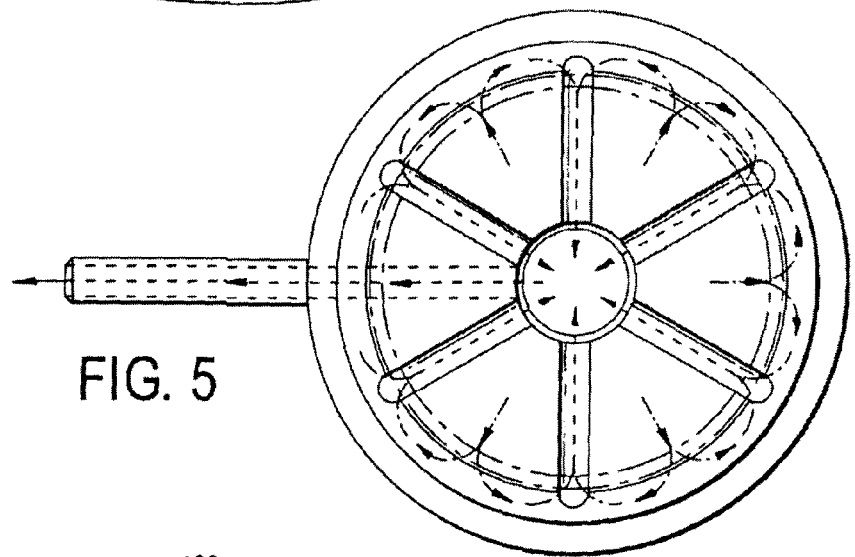
FIG. 5 is top plan view of the bottom plate of the air sampler device of FIG. 3 showing movement of air within the device.

The operation of the sampler 50 is best shown in FIGS. 5 and 6, where the arrows generally show the direction of travel of the air as it flows through the device 50. A sterilized sampler 50 is introduced into the clean room, and the top plate 100 is removed. The Petri dish 52 is inserted onto the bottom plate 150, and the top plate 100 is replaced. The air flow is then initiated for a predetermined period of time. Air is drawn into the sampler device 50 by the vacuum tube 170 through the air port 160. The central depressed portion 104 of the top plate 100 allows the air to sit before being sucked into the sampler 50. The depression 104 counteracts the turbulence which might result when a person walks close to the sampler 50 or crates a current of air that may otherwise disturb entry of the air and microbe carrying particulates.

This, in turn, creates a more laminar and isokinetic flow of air through the holes 112. The equal velocity of air flow assures a better representative sampling of particulates in the air as airflow symmetrically enters the sampler.

Once the air enters the holes 112 in the top plate, it strikes the capture material in the Petri dish 52. The air then travels up over the sides of the dish 52 and into the distal ends 159 of the slots 156 of the bottom plate 150. The air then travels down the elongated slots 156 beneath the dish 52, and enters the center well 158. The air is then sucked through the air passageway hole 162 and exits out of the vacuum air port 160. Once the predetermined period of time (which can be from 10-60 minutes or longer) has lapsed, the air flow is turned off. The top plate 100 is then raised, and the Petri dish 52 is removed for testing. The sampler 50 can then be sterilized, if desired, and a new Petri dish 52 introduced.

Accordingly, the air port 160 is in flow communication with the passageway 162, which is in flow communication with the well 158. And, the well 158 is in flow communication with the center well 158, which is in flow communication with the elongated slots 156. The distal ends 159 of the slots 156 are in flow communication with air entering the holes 112 in the top plate 100.

It is noted that a rubber gasket is not utilized between the shelf 153 of the bottom plate 150 and the side 114 of the top plate 100. The shelf 153 and the side 114 are machined to a tolerance level which, together with the weight of the top plate 100, becomes locked together with the force of the vacuum and substantially prevents any air from entering through the interface between the shelf 153 and the side 114. In addition, it is noted that the current invention eliminates the need for any material, such as a gasket, which might otherwise become contaminated, by reducing the number of metal-on-metal contact points. The entire device is substantially airtight, without the need of a gasket to seal any metal-on-metal contact points. The entire device 50 can be sterilized by heat, steam, VHP or ETO.

Furthermore, because the holes 112 in the top plate 100 are small, the elongated slots 156 and distal ends 159 can be made larger while retaining a high air flow rate through the holes 112. By having larger slots 156, distal ends 159, center well 158 and hole 162, the device 50 is less susceptible to becoming clogged. Though six slots 156 are provided in the illustrated embodiment, fewer or more slots can be provided, though preferably the slots are equally spaced about the Petri dish so that the distal ends uniformly draw air from the dish.

In accordance with the preferred embodiment of the invention, the vent plate 110 has a diameter of approximately 2.5 inches and a thickness of 0.0600 inches. The size (i.e., diameter) of the vent plate 110 is substantially smaller than the size (i.e. diameter) of the Petri dish 52, to reduce the desiccation or drying of the edges of the nutrient media. The preferred ratio is about 3:4 (i.e., 2.5 inch diameter for the vent plate 110 to a 3.25 inch diameter for the Petri dish), or that the vent plate is no larger than about 75% of the size of the Petri dish. A larger ratio creates results in an air speed which adversely affects an uneven part of the media plate since the media plate is poured agar (nutrient media), which sometimes moves up the sides of the Petri dish 52 which becomes dried.

Each hole 112 has a diameter of about 0.0070 inches (0.1778 mm), which is approximately 0.00078% of the size of the vent plate 110. Since there are 283 holes over the 2.5 inch diameter plate 110, the holes 112 account for approximately 0.22% of the area of the vent plate 110. The holes 112 are positioned in 9 concentric rings at the following diameters: 0.0 (1 hole), 0.40625 (10 holes), 0.65625 (15 holes), 0.90625 (20 holes), 1.15625 (26 holes), 1.40625 (31 holes), 1.65625 (37 holes), 1.90625 (42 holes), 2.15625 (48 holes), and 2.40625 (53 holes). It should be appreciated, however, that the size of the holes 112 can vary within the spirit of the invention, and the number of holes 112 may be more or less than 283. Preferably, however, there are at least 100-150 holes, and more preferably at least 200 holes, with each hole being 0.007-0.009 inches in diameter. Preferably, however, the holes 112 comprise less than about 1%, of the surface area of the vent plate 110 (i.e., the area in which the holes are located).

By having small holes 112 in the top plate 100, air is drawn into the sampler 50 at a high flow rate (about 67.20 m/s per hole) and volume (about 1.67E-06 $m^3$/s per hole), while keeping the flow rate at 1 CFM (or 28.3 cubic liters per minute) at the air port 160 to provide a longer sampling time. The flow rate of the air as it is drawn into the holes 112 is about 28.3 LPM or 1 CFM or through each hole 0.1 is LPM. The total for the top plate 100 is about 0.000472 $m^3$/s. Particle sizes of about 0.2-9 microns may be reflected, while 10+ microns are deposited. Particles of 0.2-9.0 microns can be swept away from dynamic drag if the airflow is too high, so that airflow is reduced to capture those smaller particulates. The sampler 50 has an efficiency loss of about 5.6-7.2%, which is much lower than conventional samplers which have an average loss of approximately 20%.

The faster air flow at the holes 112 provides higher capture realization in the material located in the Petri dish 52 since the particles can't bounce off of the capture material. The sampler 50 will capture particles which are approximately 0.5-30 g m in size. The well 158 is one inch in diameter, and about ⅜ inches deep from the top surface 152. The slots 156 are about 0.25 inches wide and the distal end 159 of the slots 156 extends ⅛ inch into the ridge 154. The ridge 154 is 0.25 inches wide. Though six slots 156 are provided, more or fewer slots can also be utilized. The sampler 50 can be utilized with the sampling system shown in WO2009/100184. The capture material in the Petri dish 52 is usually a bacterial growth medium, such as trypticase soy agar, though any suitable medium can be used. The dish 52 has a diameter of 3.5 inches and can retain 18, 25 or 32 ml of capture material, though the dish 52 can be any suitable size.

Figure 7:
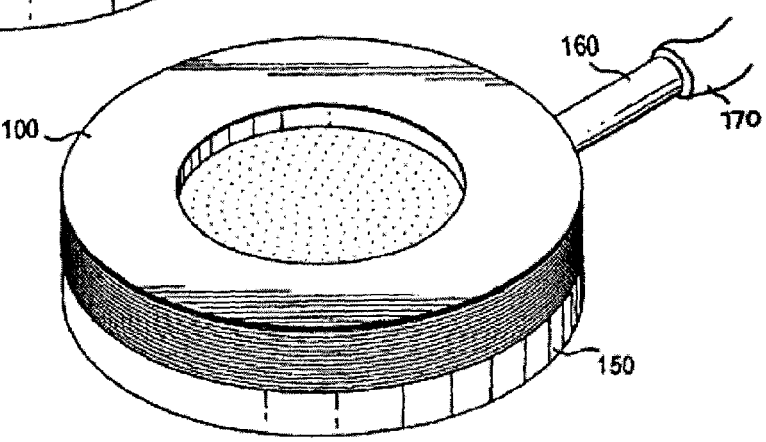

Further to the preferred embodiment, the top plate 100 and the bottom plate are both circular, with a diameter of approximately 4.5 inches. The completely assembled sampler device 50 is shown in FIG. 7. The bottom plate 150 is sized and shaped substantially the same as the top plate 100, though the top plate 100 can be slightly larger to further assist in removing it from the bottom plate 150 without disturbing the bottom plate 150. Though the device 50 is shown as circular, other shapes may be used. And, the device 50 may be substantially larger or smaller than the dimensions provided.

The plates 100, 150 are preferably made of stainless, anodized aluminum. The bottom of the sides 114 of the top plate 100, and the top shelf 153 of the bottom plate 150, are machined to a sufficient degree to provide a substantially airtight seal therebetween without the need for a gasket or other element. The plates 100, 150 are relatively heavy, so that they do not break, get knocked over, and creates a relatively airtight seal between the plates. There is approximately 0.015 inches between the outer portion of the ridge 154 and the side wall 114 of the top plate 100. In addition, a metal cover can be provided which covers the top plate 100. The cover is larger than the top plate 100, preferably with a diameter of 4⅝ inches, so that it can be easily removed from the top plate 100. The cover prevents particles from entering the device 50 when it is not being operated.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

I claim:

1. A gas sampler device comprising:
    a top plate having a top surface with a plurality of holes;
    a bottom plate forming an enclosure with said top plate, said bottom plate having an upwardly projecting ridge, said ridge defining a receiving portion for receiving a dish in said enclosure, and having a center well formed in said bottom plate;
    a plurality of elongated slots formed in said bottom plate and extending outward from said center well, each said plurality of elongated slots being in flow communication with said center well;
    a gas passageway formed in said bottom plate, and said gas passageway being in flow communication with said center well and extending through said bottom plate to outside bottom plate; and
    an air port located outside said bottom plate being in flow communication with said gas passageway, said air port configured to connect to a vacuum tube, said air port being configured to draw gas into said enclosure through said top plate to impinge on said dish and travel through said plurality of elongate slots into said well.

2. The gas sampler device according to claim 1, wherein each of said plurality of elongated slots having a proximal end in flow communication with said center well and distal end in said ridge beyond said receiving portion.

3. The gas sampler device according to claim 1, wherein said plurality of holes in less than 0.5% of said top surface of said top plate.

4. The gas sampler device according to claim 1, wherein said top plate has a top surface with a depressed portion, and said plurality of holes are located in said depressed portion.

5. The gas sampler device according to claim 1, wherein each of said plurality of holes has a diameter of approximately 0.007 to 0.009 inches.

6. The gas sampler device according to claim 1, wherein said top plate has at least one side which has a plurality of ridges, and said bottom plate has at least one side that is smooth.

7. The gas sampler device according to claim 1, wherein said plurality of elongated slots extend into said ridge.

8. The gas sampler device according claim 1, wherein said gas comprises air.

9. The gas sampler device according to claim 1, wherein the entire device is metal.

10. A gas sampler device according to claim 1, wherein said device is substantially airtight.

11. The gas sampler device according to claim 1, wherein said device does not have a gasket.

12. The gas sampler device according to claim 1, wherein said plurality of holes comprise at least 150 holes.

13. The gas sampler according to claim 1, wherein the gas sampler device is configured such that gas may be drawn into the plurality of holes at a speed of approximately 67.20 mis per hole when the volume of gas entering said plurality of holes is approximately 1.6E-06 $m^3$/s per hole.

14. A gas sampler device comprising:
    a top plate having a top surface with a plurality of holes;
    a bottom plate forming an enclosure with said top plate, said bottom plate having an upwardly projecting ridge, said ridge defining a receiving portion for receiving a dish in said enclosure, and having a center well formed in said bottom plate;
    a plurality of elongated slots formed in said bottom plate and extending outward from said center well, each of said plurality of elongated slots being in flow communication with said center well, each of said plurality of elongated slots having a proximal end in flow communication with said center well and a distal end in said ridge beyond said receiving portion;
    a gas passageway formed in said bottom plate, said gas passageway being flow communication with said center well and extending through said bottom plate to outside said bottom plate; and
    an air port located outside said bottom plate being in flow communication with said gas passageway, said air port configured to connect with connect to a vacuum tube.

15. A gas sampler device comprising:
    a top plate having a top surface with a plurality of holes;
    a bottom plate forming an enclosure with said top plate, said bottom plate having an upwardly projecting ridge, said ridge defining a receiving portion for receiving a dish in said enclosure, and having a center well formed in said bottom plate;
    a plurality of elongated slots formed in said bottom plate and extending outward from said center well, each of said plurality of elongated, slots being in flow communication with said center well, said plurality of elongated slots extending into said ridge;
    a gas passageway formed in said bottom plate, said gas passageway being in flow communication with said center well and extending through said bottom plate to outside said bottom plate; and
    an air port located outside said bottom plate being in flow communication with said gas passageway, said air port configured to connect with a vacuum tube.

\* \* \* \* \*